United States Patent [19]

Tsao

[11] Patent Number: 5,702,035
[45] Date of Patent: Dec. 30, 1997

[54] SLENDER TUBULAR CONTAINER WITH OPENING AND CLOSING MEANS

[76] Inventor: Chien-Hua Tsao, 5 Fl., No.569, Ta-Chin St., Taichung, Taiwan

[21] Appl. No.: 524,386

[22] Filed: Sep. 5, 1995

[51] Int. Cl.⁶ ................................................. B67D 3/00
[52] U.S. Cl. ................................................. 222/187
[58] Field of Search ........................... 222/187; 401/198, 401/132; 604/3, 306; 239/44

[56] References Cited

U.S. PATENT DOCUMENTS

| | | | |
|---|---|---|---|
| 3,324,855 | 6/1967 | Heimlich | 604/3 |
| 3,958,571 | 5/1976 | Bennington | 604/3 |
| 4,863,422 | 9/1989 | Stanley | 604/3 |
| 4,875,602 | 10/1989 | Chickering et al. | 222/187 |

*Primary Examiner*—Philippe Derakshani
*Attorney, Agent, or Firm*—Pro-Techtor International

[57] ABSTRACT

A tubular container includes a barrel containing liquid such as medicine or perfume. The barrel has an applicator end wrapped by an absorbing element to allow liquid to flow out while another end is sealed. Upon breaking the sealed end, atmospheric pressure will cause the liquid to flow out of the barrel through the applicator end for application. The end of the container with the absorbing element has a liquid silicone stopper disposed therein.

3 Claims, 3 Drawing Sheets

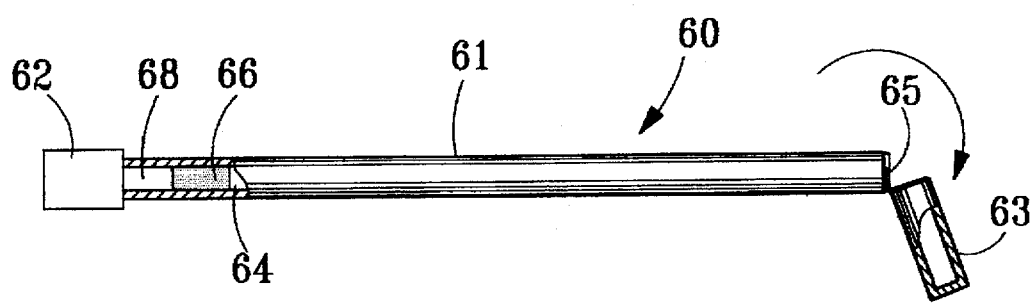
FIG. 1
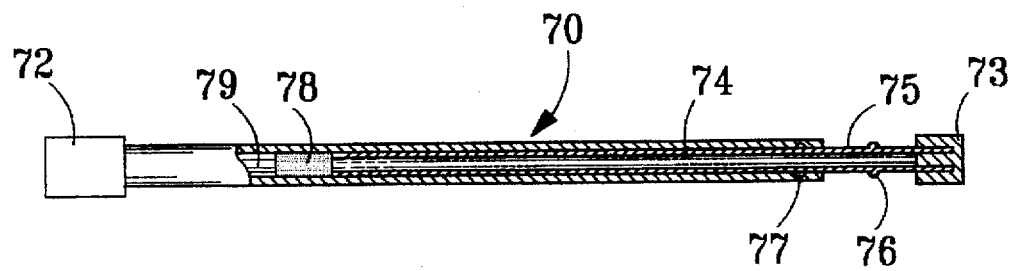
FIG. 2
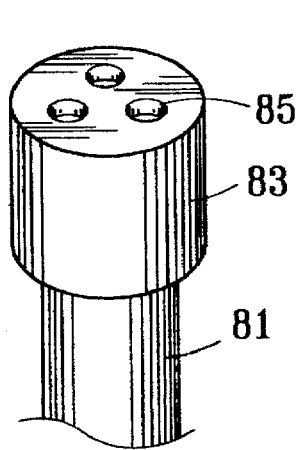 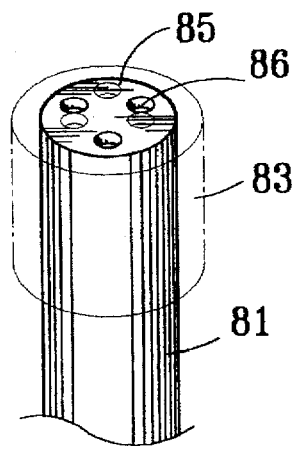 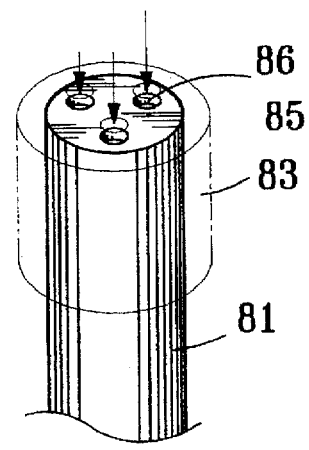
FIG. 3   FIG. 4   FIG. 5

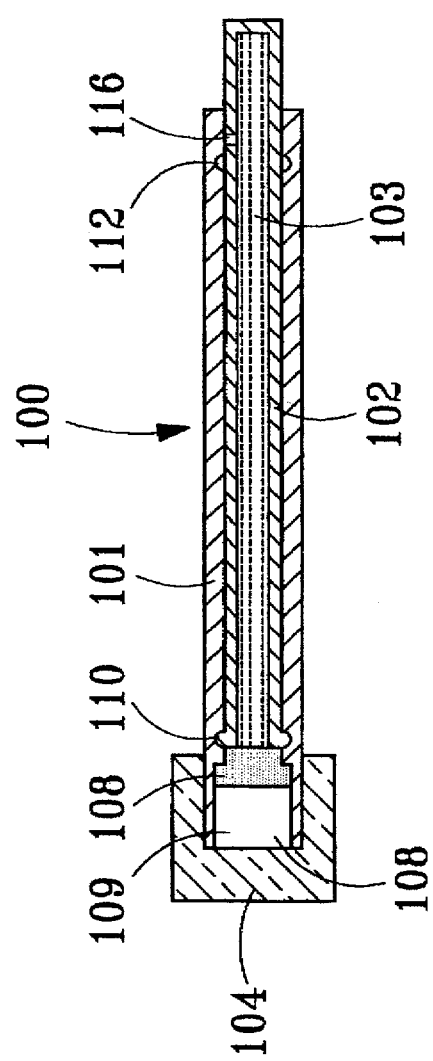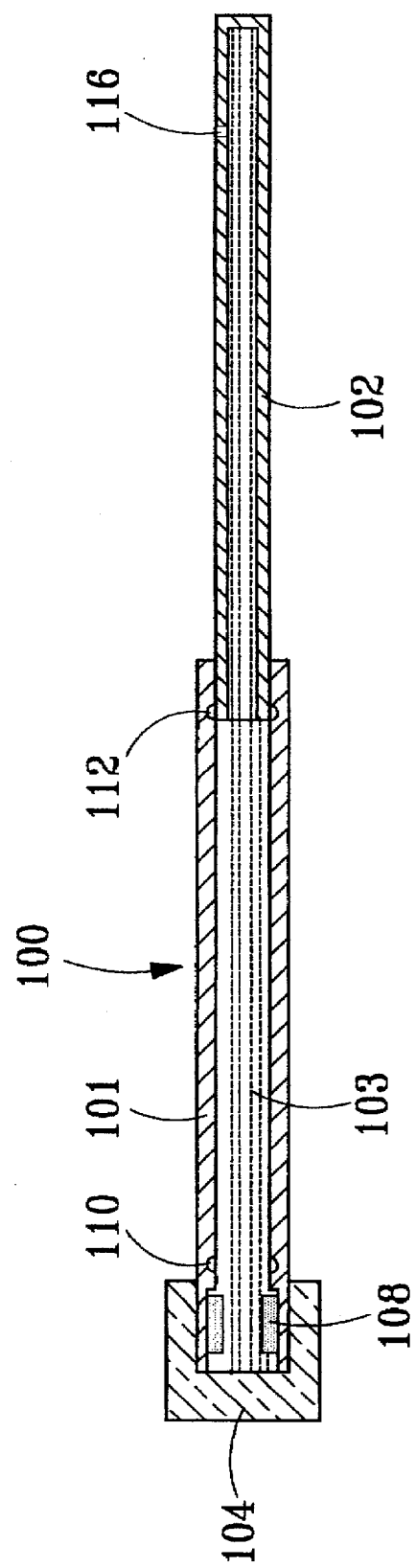

5,702,035

SLENDER TUBULAR CONTAINER WITH OPENING AND CLOSING MEANS

BACKGROUND OF THE INVENTION

1. Field of the Invention

The invention relates to a sealed container and more particularly to a slender tubular container with sealing and releasing means.

2. Description of the Prior Art

Conventional articles for treating trauma include cotton swabs to apply a variety of medicines contained in different vials. This is not a convenient method of application, particularly when time is critical. It also requires a large storage space, and it is difficult to track the various expiration dates. Therefore some of the medicines could easily expire and have to be thrown away. This is a waste of money and also causes environmental problems. Furthermore, the frequent opening and accessing of the medicine vial or cotton swab container can easily contaminate the medicine or cotton swab. This could result in harmful effects on the wound. It is also bothersome to carry a number of bottles or containers during travel or outdoor activity. There is room for improvement in this method.

SUMMARY OF THE INVENTION

It is an object of the present invention to provide a slender tubular container which ha both ends sealed so that a liquid (suck as medicine or perfume) contained therein would not evaporate. The concentration of the liquid can be maintained at a constant level as there is no evaporation loss. Furthermore the container can be packaged directly without external packaging material, thus reducing the storage space required and the cost of transportation. The liquid contents also are free from leaking, spoiling or contamination due to both ends of the container being sealed.

The production process is simple and the dosage is easy to control. According to the invention, one oend of the container is permanently sealed (the breakable end or sealed element end). The other end of the container is sealed with silicone and has an absorbing element wrapped therearound. When in use, the sealed end is broken open. The applicator end has a liquid silicone stopper disposed therein. As silicone is immiscible in water, an opening is formed in the center of the tube when lower internal contraction force and lower fluidity and the sealed end is opened, so that the liquid in the container can flow therethrough. (The viscosity of the silicone causes it to adhere to the walls of the container.) The liquid in the container flows to the application end and into the absorbing element to facilitate applying of the liquid medicine or perfume to the body. The present invention is a simple, effective and convenient medical or personal care article.

BRIEF DESCRIPTION OF THE DRAWINGS

The drawings disclose illustrative embodiments of the present invention which serve to exemplify the various advantages and objects thereof, and are as follows:

FIG. 1 is a front view, partly cutaway, of the first embodiment of the invention, FIG. 2 is a front view, partly cutaway, of the second embodiment of the invention.

FIG. 3 is a perspective view of a sealing element of the third embodiment of the invention.

FIG. 4 is a fragmentary perspective view of a barrel of the third embodiment of the invention.

FIG. 5 is a perspective view of the third embodiment of the invention with the air ventilation holes aligned.

FIG. 6 is a sectional view of the fourth embodiment of the invention showing a closed state.

FIG. 7 is a sectional view of the fourth embodiment of the invention showing an open state.

DETAILED DESCRIPTION OF THE PREFERRED EMBODIMENT

Figure 8:
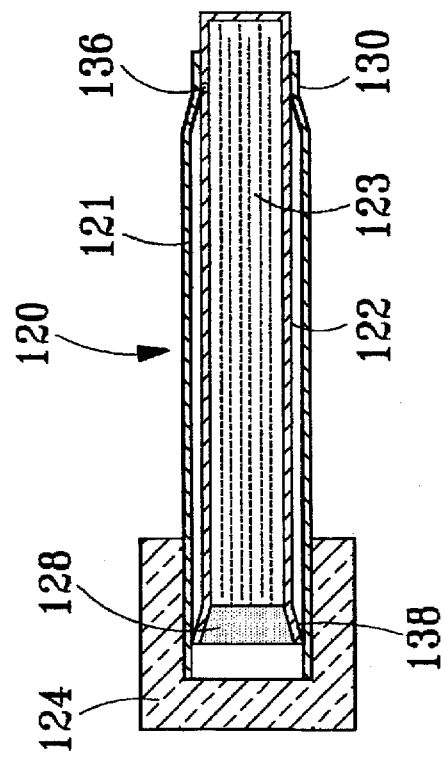
FIG. 8 is a sectional view of the fifth embodiment of the invention showing an open state.

Referring to FIG. 1, the tubular container 60 according to the present invention has a hollow barrel 61 which includes an absorbing element (applicator) 62 at an applicator end. There is a non-toxic liquid silicone stopper 66 disposed in the barrel near the applicator 62. A gap 68 is located between the absorbing element 62 and the stopper 66. A second sealed end of the barrel 61 includes a sealing element 63. There is a notch 65 formed at the connection of the sealing element 63 and the barrel 61 to allow the sealing element 63 to be easily broken from the barrel 61 of the container 60.

Liquid 64 is contained in the hollow interior of the barrel 61. When in use, the sealing element 63 is broken at the notch 65 while holding the sealed end higher than the applicator end. Atmospheric pressure then causes the liquid 64 to flow through the silicone stopper 66, the gap 68 and into the absorbing element 62. Under pressure, the silicone clings to the walls of a container, thereby forming a throughway. The absorbing element 62 which contains the liquid then can be used to apply the liquid to a human body for treatment purposes.

FIG. 2 illustrates the second embodiment of the invention. The tubular container 70 includes a barrel and a plunger 75. At one end of the barrel there is an absorbing element 72. A second end of the barrel is open and has an annular groove 77 formed in the inner circumference. The plunger 75 is inserted into the barrel 71 through the open end. There is a sealing element 73 disposed at one end of the plunger 75 located outside the barrel 71. An annular flange 76 is formed on the outer circumference of the plunger 75 near the sealing element 73 for engaging with the annular groove 77. Liquid 74 is contained in the plunger 75. There is a gap 79 and a silicone stopper 78 in the barrel 71 near the end of the absorbing element 72. When the sealing element 73 is pulled from the plunger 75, atmospheric pressure will cause the liquid to flow into the absorbing element 72 for application. Silicone 78 may also be disposed at one end of the plunger 75, then the plunger 75 and the liquid 74 contained therein may be produces separately from the barrel 71 as an independent and replaceable unit.

FIGS. 3, 4 and 5 illustrate the third embodiment of the invention. It is structured in general like the first embodiment, except that there is a sealing element 83 disposed at the sealed end of the barrel 81. There are ventilation holes 85 formed in the sealing element 83. There are also corresponding ventilation holes 86 formed in the sealed end of the barrel 81. When holes 85 and 86 do not align with each other, it is in a sealed state (a shown in FIG. 4). When the sealing element 83 is turned and the holes 85 are aligned with the holes 86 of the barrel 81 (as shown in FIG. 5), atmospheric pressure will cause the liquid contained in the barrel 81 to flow into the absorbing element for application.

FIGS. 6 and 7 illustrate the fourth embodiment of the invention. Container 100 includes a barrel 101 and a plunger 102. At one end of the barrel 101, there is an absorbing element 104, a gap 109, and a sillconic stopper 108. There are also two annular grooves 110 and 112 formed on the inside circumference of the barrel 101 near the two ends. Plunger 102 has one end sealed and another end open. There is an annular flange 118 formed on the open end and an aperture 116 formed at the sealed end of the plunger 102. Liquid 103 is contained in the plunger 102. FIG. 6 illustrates a sealed state where annular flange 118 engages wit annular groove 110 and aperture 16 is located inside the barrel 101. When in use, as shown in FIG. 7, the plunger 102 is pulled out of the barrel 11 until annular flange 118 engages with annular groove 112. As aperture 116 is exposed to the atmosphere, pressure will cause the liquid 103 to flow into the absorbing element 104 for application.

Figure 9:
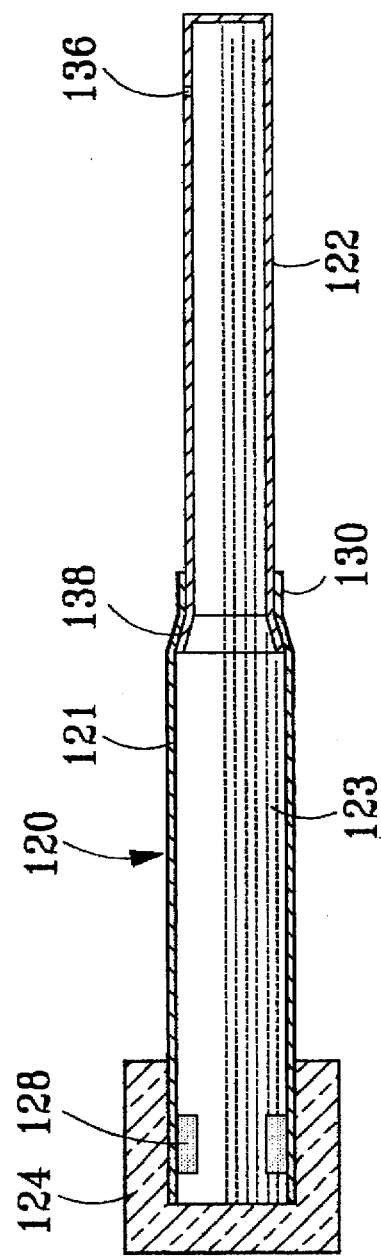
FIG. 9 is a sectional view of the fifth embodiment of the invention showing an open state.

FIGS. 8 and 9 illustrate the fifth embodiment of the invention, which is similar in structure to the fourth embodiment. The container 120 has a barrel 121 which is wrapped by an absorbing element 124 at one end while another end 130 is open and taped to allow a plunger 122 to slide therethrough. Plunger 122 has an open end 138 formed in a conical shape and matched with the tapered end of the barrel 121. There is a silicone stopper 128 disposed in the conical end 138. Another end of the plunger 122 is sealed and has an aperture 136 formed in the circumference. When the plunger 122 is placed inside the barrel 121 as shown in FIG. 8, aperture 136 is covered by the barrel 121, thus forming a sealed state. When the plunger 122 is pulled outward as shown in FIG. 9, tapered end 130 engages firmly with the conical end 138, aperture 136 is exposed, and atmospheric pressure will cause the liquid 123 held in the plunger 122 to flow through the stopper 128 and into the absorbing element 124 for application.

The absorbing element of the invention is preferably made of a polymer material which is soft, has high plasticity, a good absorbing capability and is resilient. Suitable materials are natural cotton, seed fiber, vegetable fibers, animal fibers, staple fibers, etc. The absorbing element should be properly sanitized before use. The invention can function equally well with or without the absorbing element. The silicone stopper of the invention in preferably made of silicone dioxide or the like which is non-toxic, has proper adhesiveness, and allows liquid to flow through. The tubular barrel of the invention in preferably less than 6 mm in diameter. Other dimensions may be used when desired. The liquid of the invention may be perfume, alcohol, detergent, medicine or other chemicals.

The various embodiments of the invention allow the containing liquid to be safely contained and sealed without evaporation or contamination during transportation and storage. The container can be easily and conveniently used regardless of the tube size. It is a useful article suitable for a wide variety of applications.

Many changes and modifications in the above described embodiments of the invention can, of course, be carried out without departing from the scope thereof. Accordingly, to promote progress in science and the useful arts, the invention is disclosed and is intended to be limited only by the scope of the appended claims.

I claim:

1. A tubular container containing:

a first sealed end and a second applicator end, with a tubular barrel containing liquid disposed therebetween, wherein at least said applicator end of said barrel includes a non-toxic liquid silicone stopper disposed therein, said silicone stopper is separated from said applicator end by an air gap;

wherein when said sealed end of said container is broken, said liquid flows out of said barrel through said applicator end.

2. The container of claim 1 wherein:

said sealed end of said container includes a notch to facilitate breaking of said sealed end.

3. The container of claim 1 wherein:

said applicator includes an absorbing element disposed therearound.

* * * * *

UNITED STATES PATENT AND TRADEMARK OFFICE
Certificate

Patent No. 5,702,035            Patented: December 30, 1997

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Chien-Hua Tsao, Taichung, Taiwan; and Garry Tsaur, Rowland Heights, CA.

Signed and Sealed this First Day of March 2005.

MICHAEL Y. MAR
*Supervisory Patent Examiner*
Art Unit 3754